(12) United States Patent
Williams

(10) Patent No.: US 10,438,475 B2
(45) Date of Patent: Oct. 8, 2019

(54) BED MONITORING PAD

(71) Applicant: Rondish Company Limited, Kwai Chung, N.t (TW)

(72) Inventor: Steven Alfred Williams, Kwai Chung (HK)

(73) Assignee: Rondish Company Limited, Kwai Chung, N.T. (HK)

( * ) Notice: Subject to any disclaimer, the term of this patent is extended or adjusted under 35 U.S.C. 154(b) by 257 days.

(21) Appl. No.: 15/272,773

(22) Filed: Sep. 22, 2016

(65) Prior Publication Data

US 2017/0092103 A1 Mar. 30, 2017

Related U.S. Application Data

(60) Provisional application No. 62/232,232, filed on Sep. 24, 2015.

(51) Int. Cl.
| | |
|---|---|
| A61B 5/11 | (2006.01) |
| G08B 21/22 | (2006.01) |
| A61B 5/00 | (2006.01) |
| A61G 5/10 | (2006.01) |
| A61G 7/05 | (2006.01) |

(52) U.S. Cl.
CPC ............ G08B 21/22 (2013.01); A61B 5/1115 (2013.01); A61B 5/6892 (2013.01); *A61G 5/1091* (2016.11); *A61G 7/0527* (2016.11); *A61G 2203/32* (2013.01); *A61G 2203/34* (2013.01); *A61G 2203/44* (2013.01)

(58) Field of Classification Search
CPC ........................................................ A61B 5/11
USPC .............................................. 340/573.1, 575
See application file for complete search history.

(56) References Cited

U.S. PATENT DOCUMENTS 5,796,059 A * 8/1998 Boon ..................... A61B 5/1115
                                                              200/85 R
6,696,653 B1 * 2/2004 Smith ..................... H01H 3/142
                                                              200/85 R

* cited by examiner

*Primary Examiner* — Fredrick C Conley
(74) *Attorney, Agent, or Firm* — Mintz Levin Cohn Ferris Glovsky and Popeo, P.C.

(57) ABSTRACT

A sensor pad is adapted to be positioned under a mattress of a patient's bed as part of a monitoring system that provides a signal to a caregiver when the patient rises from the bed can be used for multiple patients. The under-mattress sensor pads can be used for a long period of time as the under-mattress sensor pads includes a relatively stiff material.

9 Claims, 7 Drawing Sheets

Standard Pad
Normally Used On
Top of Mattress

BED MONITORING PAD

CROSS REFERENCE TO RELATED APPLICATION

This application claims priority under 35 U.S.C. § 119(e) to U.S. Provisional Patent Application Ser. No. 62/232,232, titled "Bed Monitoring Pad," filed Sep. 24, 2015, the disclosure of which is hereby incorporated by reference in its entirety.

BACKGROUND

The present disclosure relates to a sensor pad, in particular, a pad for detecting when an individual exits a chair or a bed.

A serious problem encountered by operators of hospitals, nursing homes, retirement centers, and other facilities that care for patients with limited mobility is that patients who leave their beds without assistance may subsequently trip or fall. Patients that are heavily medicated or sedated are particularly susceptible to falls. For these reasons, much consideration has been given to systems for monitoring patients and providing a warning that a patient is rising from or has left his or her bed.

One type of currently used sensor pad is one that is positionable on a mattress of a bed or seat of a chair. The sensor pad is communicatively coupled to a monitoring device, such as a nurse call system. When pressure on the sensor pad is removed, such as when the patient removes himself or herself from the bed or chair, the sensor pad sends a notification to the monitoring device which provides a notification to the caregiver that the patient is no longer in bed or seated in the chair.

Currently, most of the sensor pads used in patient beds are placed above the mattress in a patient bed. Because of this positioning, current patient monitoring sensor pads are made of soft materials, that are comfortable to sit or lay on, and are more frequently exposed to fluids, friction, and other situations that may reduce the longevity of the monitoring sensor pads.

Described below are patient monitoring sensor pads that are robust and made for placement under the mattress of a patient's bed.

SUMMARY

Disclosed is a patient monitoring pad that can be placed underneath the mattress in a patient's bed. The patient monitoring sensor pad can be used for multiple patients and over an extended period of time before degradation in the performance of the monitoring pad.

In one aspect, the bed monitoring pad comprises a flexible first plate with conductive material printed thereon; a flexible second plate with conductive material printed thereon, wherein the first flexible plate and second flexible plate comprise zones of conductivity; a soft sponge layer positioned between the first plate and the second plate, the soft sponge layer including a plurality of elongated openings, wherein each elongated opening extends along an axis, and wherein the axis of each elongated opening is diagonal to a long axis of the sponge layer, and wherein the zone of conductivity of the first plate is configured to make physical and electrical contact with the zone of conductivity of the second plate through the opening in the sponge layer when a patient sits or lies on the bed monitoring pad; and a bottom layer below the second plate, the bottom layer being more rigid than the first and second.

Other features and advantages should be apparent from the following description of various embodiments, which illustrate, by way of example, the principles of the disclosure.

DETAILED DESCRIPTION

A patient monitoring sensor pad that is configured for use under the mattress of a patient's bed or under the cushion of a patient's chair is described. The patient monitoring sensor pad is made of robust materials and is configured for use with multiple patients, as well as for a long lifetime. Also described are systems that include such patient monitoring sensor pads, as well as methods of using such patient monitoring sensor pads.

Figure 1A:
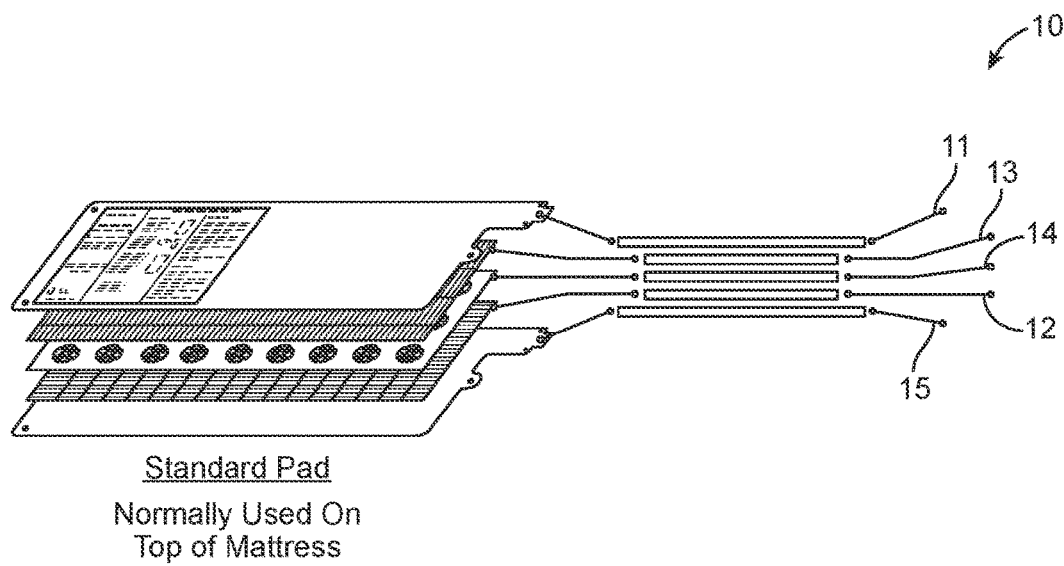
FIG. 1A is a schematic of a conventional mattress patient monitoring sensor pad, showing the materials in the pad and how they are arranged.
Figure 1B:
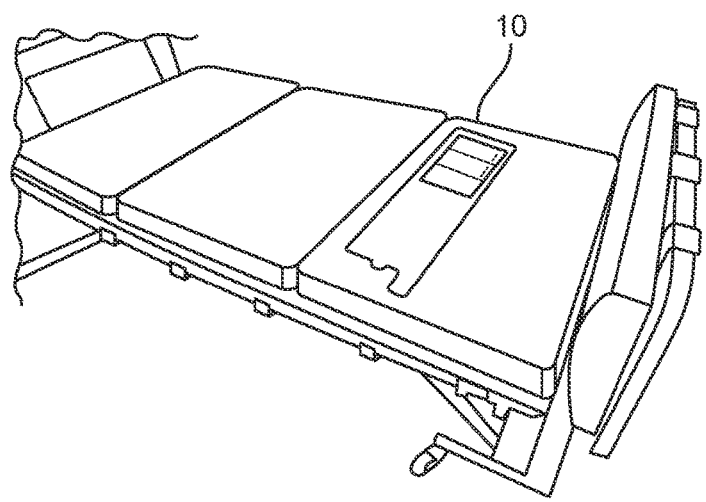
FIG. 1B shows the patient monitoring sensor pad of FIG. 1A positioned atop a bed mattress.

FIG. 1A shows a conventional patient monitoring sensor pad 10. FIG. 1B shows the conventional sensor pad 10 positioned atop a bed mattress. The conventional patient monitoring sensor pad 10 is configured for use on top of the mattress or cushion on which a patient lays or sits. Because the conventional patient monitoring sensor pad 10 is designed to be in close contact with a patient who lays atop the mattress, at times only separated by a sheet or thin layer of bedding, the conventional sensor pad 10 is made for patient comfort. What this means is that conventional patient monitoring sensor pads are made to be thin and soft. As a result, conventional patient monitoring sensor pads are flexible and bend easily. Also, the human body and variances in the shape and weight distribution of the body are relied upon for proper indications of the presence or absence of a patient.

In FIG. 1A, the conventional patient monitoring sensor pad 10 is shown as having five layers. The top 11 and bottom 15 layers can be for example Polyvinyl chloride (PVC), though any flexible, soft, durable, and water resistant material can be used. Between the top 11 and bottom 15 layers are two contact plates 13 and 12 that have a soft sponge 14 between them. The contact plates 13 and 12 can be hard thin plastic with a metallic or carbon coated layer.

A conventional patient monitoring sensor pad 10 is in reality not comfortable to lay on, and the conventional sensor pad can move as the patient moves, possibly moving the sensor pad into an undesirable position. Hygiene can also be a concern with conventional patient monitoring sensor pads because of the proximity to the patient and bodily fluids. Being on top of a patient's mattress or cushion can also expose the sensor pad to other conditions that could reduce the lifetime of the sensor pad. In some hospitals, conventional patient monitoring sensor pads are changed when a new patient occupies a bed because of the hygienic concerns.

Figure 2A:
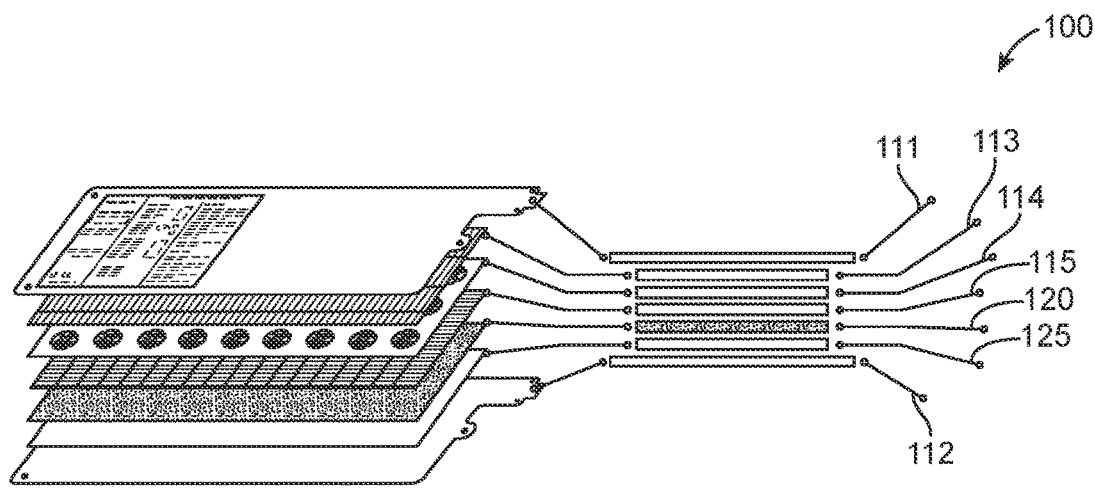
FIG. 2A is a schematic of a first embodiment of an under-mattress patient monitoring sensor pad, showing the materials in the pad and how they are arranged.
Figure 2B:
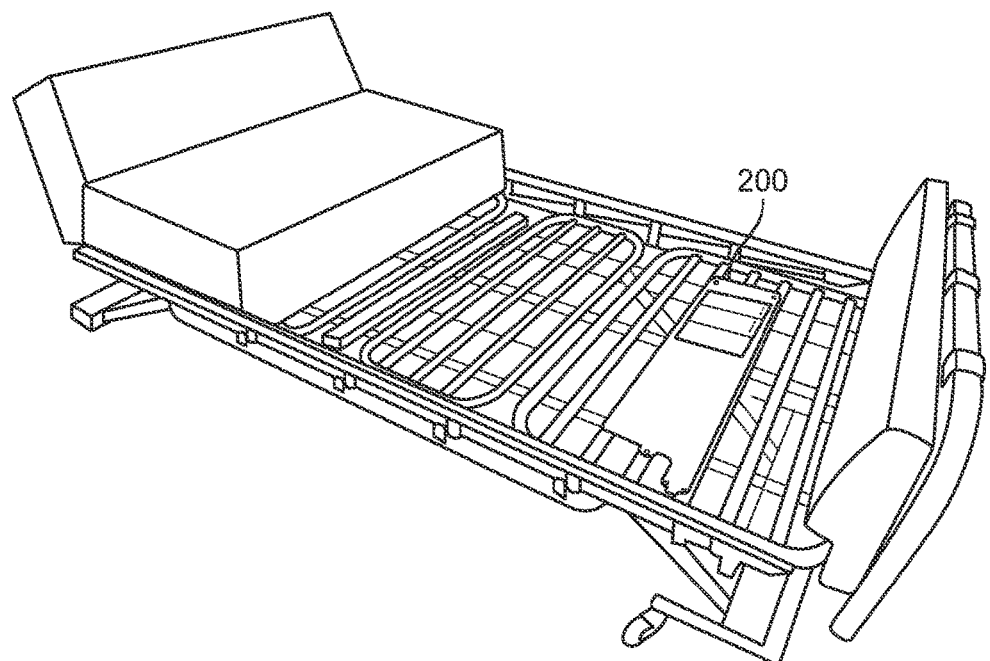
FIG. 2B shows the patient monitoring sensor pad of FIG. 2A positioned atop a bed frame atop which a mattress is to be positioned.

FIG. 2A also shows a first exemplary embodiment of an under-mattress patient monitoring sensor pad 100. FIG. 2B shows the under-mattress patient monitoring sensor pad 100 positioned atop a bed frame atop which a mattress would be positioned. The bed frame has a plurality of slats or struts that extend across one side rail of the bed frame to the other, opposite side rail of the bed frame. The slats are thus positioned to extend orthogonal (i.e., at a right angle) relative to a long axis of the bed frame. This leaves orthogonal, elongated slots or openings between the slats. The side rails extend parallel to the long axis of the bed frame. As mentioned, in use a bed mattress is positioned atop the bed frame such that the patient monitoring sensor pad 100 is positioned between the slats of the bed frame and the mattress.

The configuration of the under-mattress patient monitoring sensor pad 100 accommodates the environment beneath a mattress or cushion. The under-mattress patient monitoring sensor pad 100 has more layers than the conventional patient monitoring sensor pad 10. The outer most layers 111 and 112 of the under-mattress patient monitoring sensor pad 100 can be for example PVC, but these layers 111 and 112 can be made of any flexible, soft, durable, and preferably water resistant material. Immediately above the bottom layer 112 are a hard bottom plastic plate 125 and a heavy and/or rigid sponge or plastic plate 120. The rigid materials used to make the bottom plastic plate 125 and the heavy/rigid sponge/plastic plate 120 are selected to prevent the slats or strutted frame of a patient bed from causing false alarms or a non-functioning state in the sensor pad. In an embodiment, at least one of the layers below the contact plates is more rigid than either the contact plate(s) or the sponge layer. In an embodiment, a bottom most later of the pad is sufficiently rigid such that it will not deform when a patient of at least 200 pounds lies on the mattress above the pad. Below the top layer 111 and above the heavy/rigid sponge or plastic plate 120 are two contact plates 113 and 115 and a soft sponge layer 114 positioned therebetween. The layer 114 may have openings extending therethrough to permit the contact plates 113 and 115 to contact one another through the openings when a force is applied to the pad, such as when a patient lays on the mattress. The contact plates may be made of a flexible material such that they can at least partially flex or deform and contact one another through the openings in the layer 114. An electrically conductive material is printed on the contact plates.

Figure 3:
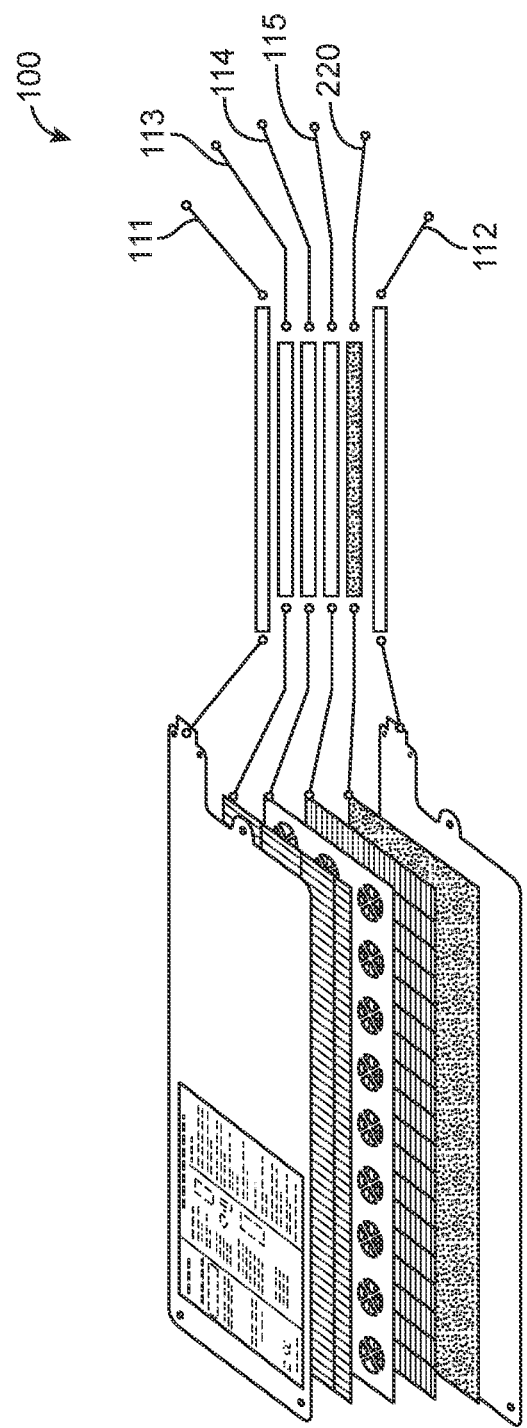
FIG. 3 is a schematic of a second embodiment of an under-mattress patient monitoring sensor pad, showing the layers or materials in the pad and how they are arranged.

FIG. 3 shows a second exemplary embodiment of an under-mattress patient monitoring sensor pad 200. Like the under-mattress patient monitoring sensor pad 100 shown in FIG. 1, the under-mattress patient monitoring sensor pad 200 has outer most layers 111 and 112 that surround two contact plates 113 and 115 and a soft sponge layer 114. The soft sponge layer 114 has openings that allow the two contact plates 113 and 115 to come in contact and close a circuit when sufficient pressure is placed on the sensor pad, such as when a patient lays on the mattress. A heavy/rigid sponge or plastic plate 220 separates the bottom layer 112 from the contact plates 113 and 115 and soft sponge layer 114.

The under-mattress patient monitoring sensor pad configuration shown in FIG. 2A and FIG. 3 accommodate the environment beneath a mattress or cushion. In an non-limiting example, the patient sits or lays six inches (15 cm) or more above the under-mattress patient monitoring sensor pad, and the mattress or cushion distributes the patient's weight in a way that is not accomplished by conventional sensor pads. As mentioned above, to prevent false alarms or a non-functioning sensor pad, the bottom portion of the under-mattress patient monitoring sensor pad is made with rigid layers beneath the detection layers (e.g. the detection layers 113, 114, 115 in FIG. 2A and FIG. 3). The rigid layers (such as the bottom-most layers 125, 220 and/or 112) make a level or flat surface below the detection layers, no matter what the type of support is under the mattress or cushion.

The configurations for under-mattress patient monitoring sensor pads described above leave the top portion of the sensor pads soft, to be able to react to changes in the weight above the sensor pad. The flexibility in the detection layers (e.g. layers 113, 114, 115 in FIG. 2A and FIG. 3) allows the sensor plates 113 and 115 to contact at the openings in the sponge layer 114 when a patient lays or sits on the mattress or cushion above the sensor pad.

Figure 4:
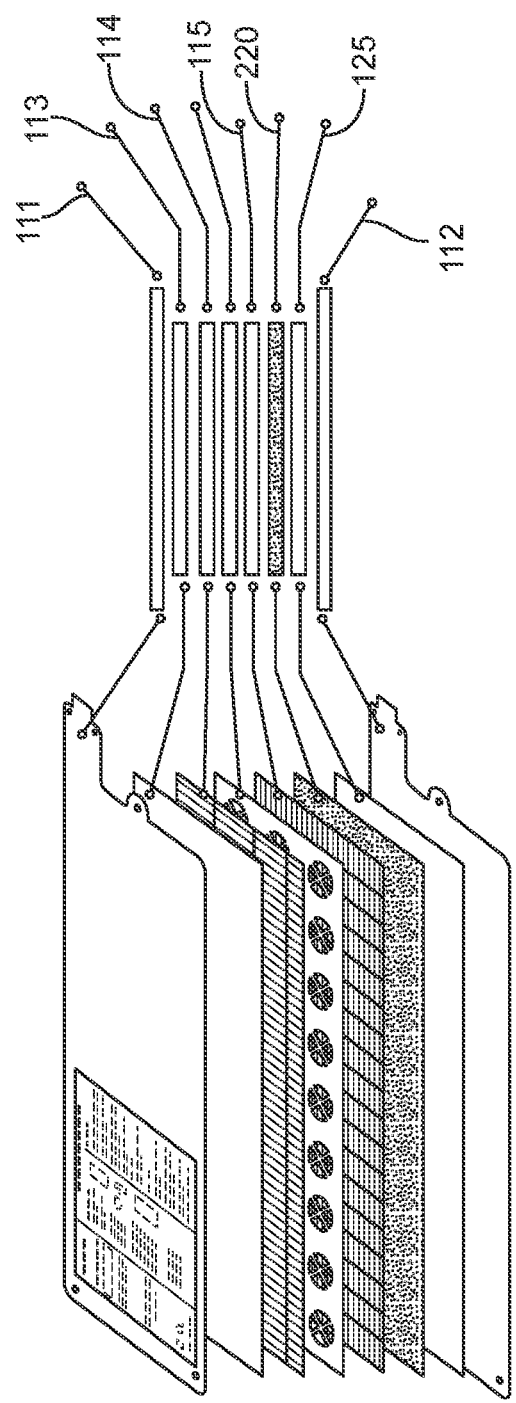
FIG. 4 is a schematic of a third embodiment of an under-mattress patient monitoring sensor pad, showing the materials in the pad and how they are arranged.

FIG. 4 shows another embodiment of an under mattress pad 300 that includes an additional hard layer of material between the upper PVC layer 11 and the contact plate 114.

Figure 5:
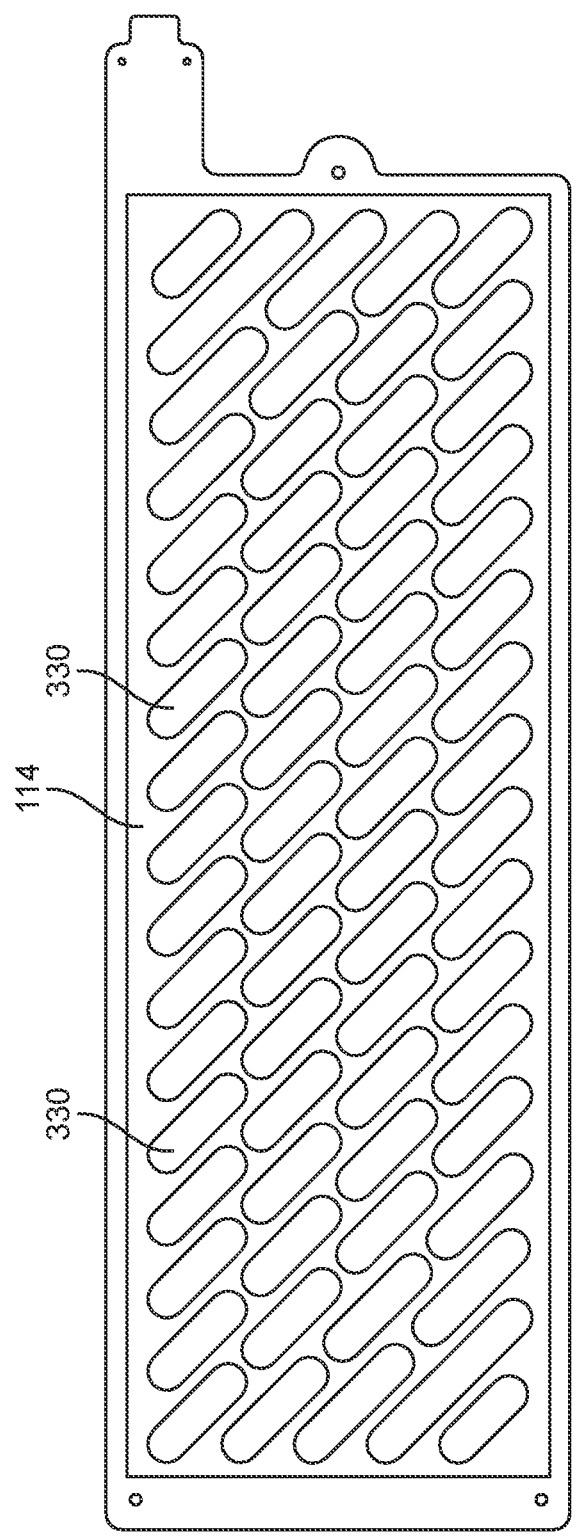
FIG. 5 is a schematic of the pattern of openings in a soft sponge layer that could be part of an under-mattress patient monitoring sensor pad.
Figure 6:
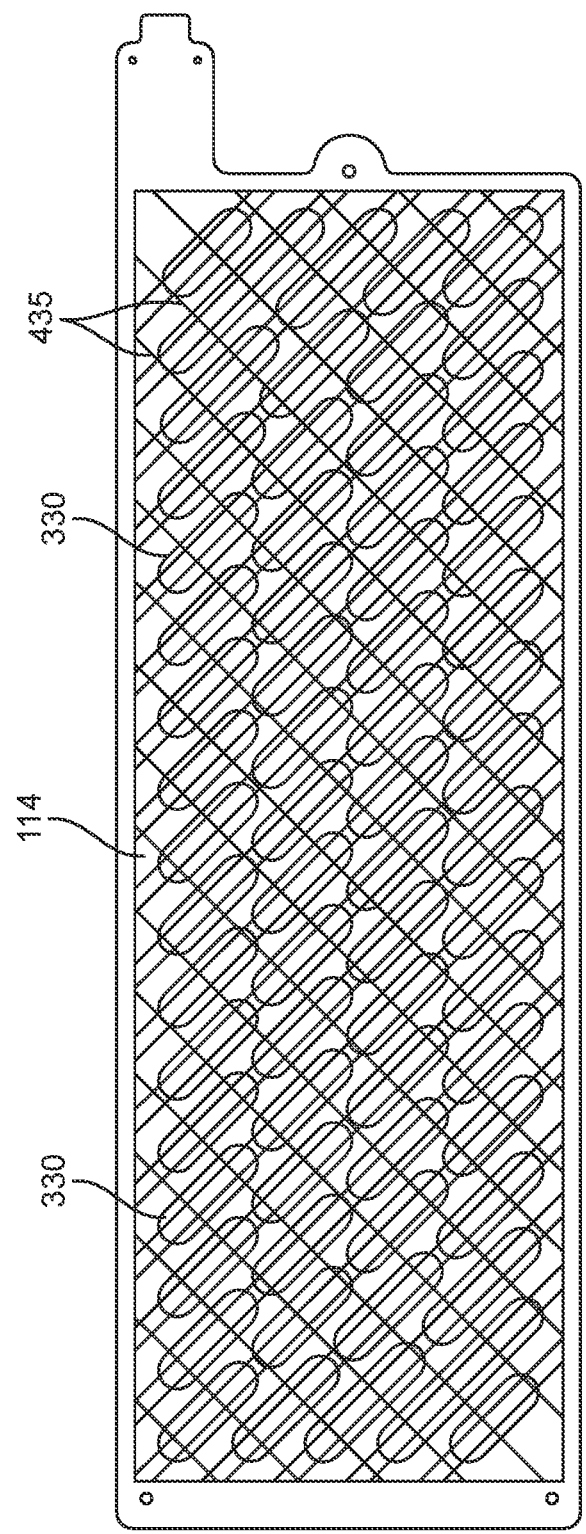
FIG. 6 is a schematic of an exemplary pattern of conducting material printed on a plate that could be part of an under-mattress patient monitoring sensor pad.
Figure 7:
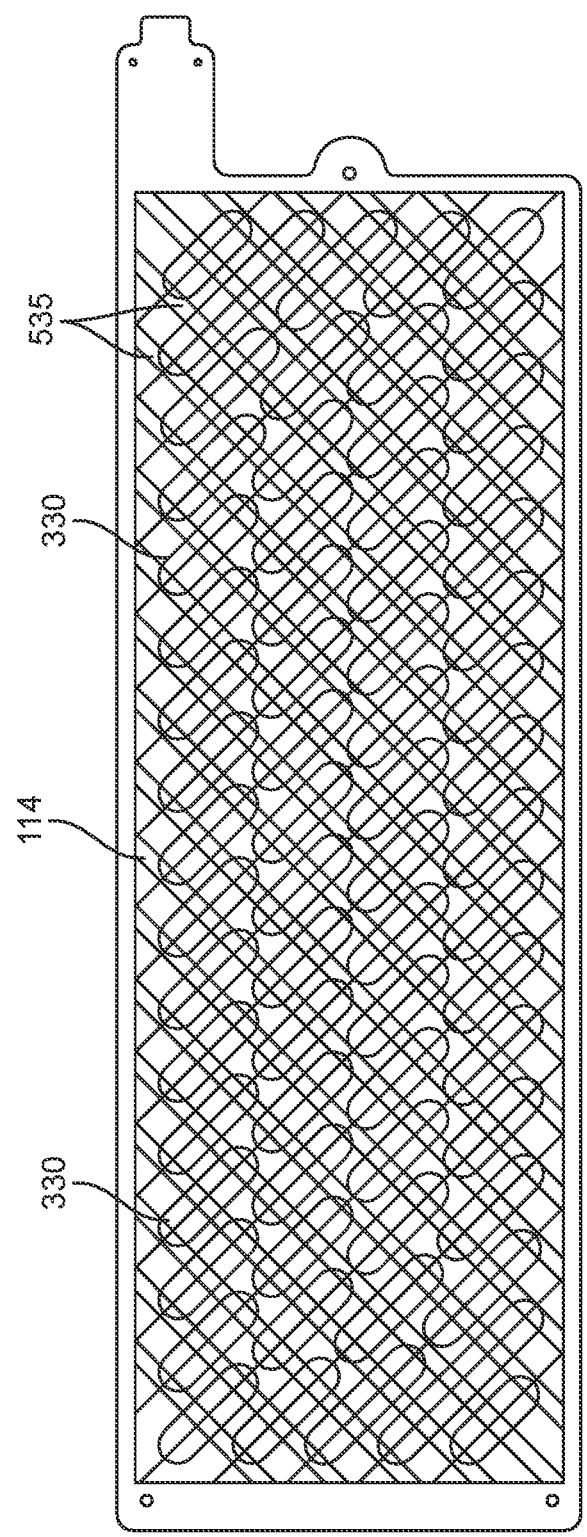
FIG. 7 is another schematic of an exemplary pattern of conducting material printed on a plate that could be part of an under-mattress patient monitoring sensor pad.

FIG. 5 shows an example sponge layer 114 with openings 330. The sponge layer is a thin substrate of material with the openings 330 therethrough. The openings are elongated slots that extend along an axis. At least some of the openings 330 extend along an axis that is diagonal with respect to a long axis of the sponge layer 114. In use, the pad is positioned so that the openings are diagonal relative to the slats or struts of the bed. The slats or struts that are used or often used in patient beds to support mattresses are usually orthogonal or at right angles to the long axis of the sponge layer 114. Positioning the openings 330 diagonally avoids false alarms or sensor pad failure due to the pressure from the slats or struts in the mattress support structure hitting a closed portion of the sponge layer 114 as opposed to an opening 330. Points in the bottom of the sensor pad in contact with the support frame often experience the most pressure when a patient sits or lays on a mattress in a patient bed. Positioning openings 330 so they are more likely to fall over those points that receive the most pressure increases the likelihood of the sensor plates 113 and 115 touching when a patient is in the bed, to give an accurate bed occupancy signal. FIGS. 6 and 7 show a sponge layer 114 with its openings 330 overlaid with patterns of conductive material 435 and 535, which are located on the sensor plates 113 and 115.

An under-mattress patient monitoring sensor pad can include circuitry to detect contact between the sensor plates 113 and 115. Also, circuitry can be included in a under-mattress patient monitoring sensor pad that signals a nurse call system once the absence of contact between the sensor plates is detected, and the patient is standing up or otherwise not laying or sitting on the mattress over the under-mattress patient monitoring sensor pad.

When using an under-mattress patient monitoring sensor pad, as described herein, the sensor pad should sit beneath the patient's hips under the mattress. Detection of the patient is best when the under-mattress patient monitoring sensor pad sits under the patient's hip. However, because patients vary in size and can move about in bed, an under-mattress patient monitoring sensor pad can be large enough to accommodate a wide range of patients. The fact that an under-mattress patient monitoring sensor pad is not subject to questionable hygiene situations as often and can be made of more robust materials allows for an under-mattress patient monitoring sensor pad as described above to be used for multiple patients, as well as for longer periods of time, for example multiple months or a year.

It should be appreciated that the sensor pad is not limited to use with a bed or bed mattress. The sensor pad can be used in combination with any item that a patient lays on or sits in, including a bed, chair, couch, and the like. In this regards, the size and shape of the sensor pad can vary to suit the item with which it is used.

Moreover, although described in the context of use with a nursing station, it should be appreciated that the sensor pad can be used in any situation where monitoring of a patient or individual is desired. For example, the sensor pad can be communicatively coupled to a Personal Emergency Alarm System (PERS) for on-site assisted living accommodation to a nurses station or off-site alarm relay via the telephone network or internet to family, friends, caregivers, control centers, or any combination thereof. The sensor pads can also be communicatively coupled with Nursecall Systems in hospitals, nursing homes, and other assisted living facilities.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, methods of use, embodiments, and combinations thereof are also possible. Therefore the spirit and scope of the appended claims should not be limited to the description of the embodiments contained herein.

What is claimed is:

1. A bed monitoring pad system, comprising:
    a flexible first plate with conductive material printed thereon;
    a flexible second plate with conductive material printed thereon, wherein the first flexible plate and second flexible plate comprise zones of conductivity;
    a soft sponge layer positioned between the first plate and the second plate, the soft sponge layer including a plurality of elongated openings, wherein each elongated opening extends along an axis, and wherein the axis of each elongated opening is diagonal to a long axis of the sponge layer, and wherein the zone of conductivity of the first plate is configured to make physical and electrical contact with the zone of conductivity of the second plate through the opening in the sponge layer when a patient sits or lies on the bed monitoring pad, wherein each elongated opening is overlaid with crisscrossing patterns of conductive material; and
    a bottom layer below the second plate, the bottom layer being more rigid than the first and second.

2. The bed monitoring pad of claim 1, wherein the bottom layer is Polyvinyl chloride.

3. The bed monitoring pad of claim 1, further comprising a plastic layer between the bottom layer and the second plate.

4. The bed monitoring pad of claim 1, further comprising a top-most layer above the first layer.

5. The bed monitoring pad of claim 1, wherein the top-most layer is Polyvinyl chloride.

6. The bed monitoring pad of claim 1, further comprising a bed frame, the bed frame being formed of a pair of side rails and a plurality of struts connecting the side rails, wherein the pad is positioned on the bed frame such that the axis of each elongated opening of the sponge layer is diagonal relative to a long axis of each strut.

7. The bed monitoring pad of claim 6, further comprising a mattress positioned atop the bed frame such that the pad is positioned between the mattress and the bed frame.

8. A method of using a bed monitoring pad, comprising:
    positioning a bed pad atop a bed frame, the bed pad comprising:
        (a) a flexible first plate with conductive material printed thereon; and
        (b) a flexible second plate with conductive material printed thereon, wherein the first flexible plate and second flexible plate comprise zones of conductivity;
        (c) a soft sponge layer positioned between the first plate and the second plate, the soft sponge layer including a plurality of elongated openings, wherein each elongated opening extends along an axis, and wherein the axis of each elongated opening is diagonal to a long axis of the sponge layer, and wherein the zone of conductivity of the first plate is configured to make physical and electrical contact with the zone of conductivity of the second plate through the opening in the sponge layer when a patient sits or lies on the bed monitoring pad, wherein each elongated opening is overlaid with crisscrossing patterns of conductive material;
    arranging the bed pad such that the axis of each elongated opening of the sponge layer is diagonal relative to a long axis of at least one strut of the bed frame.

9. The method of claim 8, further comprising positioning a mattress atop the bed frame such that the pad is positioned between the mattress and the bed frame.

* * * * *